United States Patent [19]

McLeod et al.

[11] Patent Number: 4,993,413

[45] Date of Patent: Feb. 19, 1991

[54] METHOD AND APPARATUS FOR INDUCING A CURRENT AND VOLTAGE IN LIVING TISSUE

[75] Inventors: Kenneth J. McLeod, Setauket; Clinton T. Rubin, Port Jefferson, both of N.Y.

[73] Assignee: The Research Foundation of State University of New York, Albany, N.Y.

[21] Appl. No.: 247,965

[22] Filed: Sep. 22, 1988

[51] Int. Cl.$^5$ .................................................. A61N 1/00
[52] U.S. Cl. .................................. 128/419 F; 128/421; 600/9; 600/13
[58] Field of Search .................. 128/419 F, 421, 423, 128/802, 804; 600/9, 10, 13, 14

[56] References Cited

U.S. PATENT DOCUMENTS

| | | | |
|---|---|---|---|
| 3,893,462 | 7/1975 | Manning | 128/421 |
| 4,066,065 | 1/1978 | Kraus | 128/419 F |
| 4,105,017 | 8/1978 | Ryaby et al. | 128/419 F |
| 4,266,532 | 5/1981 | Ryaby et al. | 128/419 F |
| 4,266,533 | 5/1981 | Ryaby et al. | 128/419 F |
| 4,313,438 | 2/1982 | Greatbatch | 128/419 F |
| 4,315,503 | 2/1982 | Ryaby et al. | 128/419 F |
| 4,421,115 | 12/1983 | Kraus | 128/419 F |
| 4,456,001 | 6/1984 | Pescatore | 128/419 F |
| 4,459,988 | 7/1984 | Dugot | 128/419 F |
| 4,467,808 | 8/1984 | Brighton et al. | 128/419 F |
| 4,467,809 | 8/1984 | Brighton et al. | 128/419 F |
| 4,501,265 | 2/1985 | Pescatore | 128/419 F |
| 4,519,394 | 5/1985 | Black et al. | 128/419 F |
| 4,520,360 | 7/1985 | Duarte | 128/419 F |
| 4,527,550 | 7/1985 | Ruggera et al. | 128/419 F |
| 4,535,775 | 8/1985 | Brighton et al. | 128/419 F |
| 4,548,208 | 10/1985 | Niemi | 128/419 F |
| 4,549,547 | 10/1985 | Brighton et al. | 128/419 F |
| 4,550,714 | 11/1985 | Talish et al. | 128/419 F |
| 4,556,051 | 12/1985 | Maurer | 128/419 F |
| 4,561,426 | 12/1985 | Stewart | 128/419 F |
| 4,672,951 | 6/1987 | Welch | 128/421 |
| 4,674,482 | 6/1987 | Waltonen et al. | 128/419 F |
| 4,757,804 | 7/1988 | Griffith et al. | 128/419 F |

FOREIGN PATENT DOCUMENTS 1245315 1/1984 U.S.S.R. .

OTHER PUBLICATIONS

McLeod, et al., Detection of Low Frequency Electric Fields in Physiological Systems, 1987.

(List continued on next page.)

Primary Examiner—Lee S. Cohen
Assistant Examiner—Scott M. Getzow
Attorney, Agent, or Firm—Hoffmann & Baron

[57] ABSTRACT

A method for surgically non-invasively inducing, by a time-varying magnetic field, an electrical current and voltage in living tissue, and in particular bone tissue, to prevent osteoporosis and to enhance new bone formation, includes the step of applying a symmetrical signal of low intensity and low frequency to the tissues being treated. The frequency of the induced signal is between about 1 Hertz and 1 K Hertz, and is optimally set at 15 Hertz. The peak intensity of the signal corresponds to a peak value of the inducing time-varying magnetic field of between about 0.5 millitesla per second and 5 Tesla per second, and for a 15 Hertz signal optimally corresponds to a value of 2.5 millitesla per second. A device for inducing such a signal in a limb of a person being treated includes a portable power supply in the form of a battery, a portable signal generator connected to the battery and a multiconductor ribbon cable connected to the signal generator. The multi-conductor ribbon cable has a female connector on one end and a male connector on another end. The female and male connectors are coupled together but are offset laterally from each other to provide at least one free pin on the male connector and at least one free plug on the female connector, so that the multi-conductor ribbon cable defines a single conductor treatment coil of multiple turns. The free pin and the free plug are connected to the signal output terminals of the signal generator.

8 Claims, 3 Drawing Sheets

FOREIGN PATENT DOCUMENTS

McLeod, et al., Frequency Dependence of Electric Field Modulation of Fibroblast Protein Synthesis, Jun. 1987, pp. 1465–1469.

McLeod, et al., Correlation of In-Vitro Bone Surface Potentials with Remodeling Activity in the Isolated Avian Ulna Model, 1987.

McLeod, et al., Sensitivity of Bone Remodelling Activity to the Frequency of Induced Electric Fields, 1986.

McLeod, et al., Optimization of Induced Electric Field Frequency in the Prevention of Osteoporosis, 1987.

McLeod, et al., Low Frequency Resonances Recorded In-Vivo in Functionally Loaded Bone, 1987.

McLeod, et al., Time-Varying Magnetic Fields: Effect on DNA Synthesis, 1984, pp. 818–820.

Biological and Human Health Effects of Extremely Low Frequency Electromagnetic Fields, 1985.

Assessments and Viewpoints on the Biological and Human Health Effects of Extremely Low Frequency (ELF) Electromagnetic Fields, 1985.

METHOD AND APPARATUS FOR INDUCING A CURRENT AND VOLTAGE IN LIVING TISSUE

BACKGROUND OF THE INVENTION

1. Field of the Invention

This invention relates to the treatment of living tissues and/or cells by altering their interaction with charged species in their environment. More particularly, the invention relates to an electromagnetic body treatment device and method for surgically non-invasive modification of the growth, repair and maintenance behavior of living tissues and cells by a specific and selective change in their electrical environment. Still more particularly, this invention provides for the application by a surgically non-invasive direct inductive coupling of an electrical voltage and current signal of a highly specific frequency and power, for the prevention of osteoporosis or the enhancement of new bone tissue formation.

2. Description of the Prior Art

Ryaby, et al. U.S. Pat. Nos. 4,105,017, 4,266,532, 4,266,533 and 4,315,503 collectively describe means and methods for effecting surgically non-invasive direct inductive coupling to an afflicted body region, whereby one or more electric voltage and concomitant current signals conform to a highly specific pattern and are said to have been found to develop therapeutically beneficial treatment of the afflicted region, as for example in the enhancement of repair of bone fractures, non-unions, and the like.

The methods described in one or more of the above mentioned Ryaby, et al. patents employ an asymmetrical waveform which is induced in the tissue or cells by the alternate energization and de-energization of an electromagnetic coil. FIGS. 5a and 5b of the drawings of each of the above Ryaby, et al. patents illustrate such typical asymmetrical waveforms which are induced in the tissue or cells.

For example, in what Ryaby, et al. describe in U.S. Pat. No. 4,315,503 as a Mode 1 signal (illustrated by FIG. 5a of the '503 patent), the asymmetrical waveform includes positive pulse portions P1 comprising three segments 39, 40 and 41, and a negative pulse portions P2. The frequency of the Mode 1 signal is described as being about 10 to 100 Hertz with a duty cycle of 20 to 30 percent. The average amplitude of the negative portion of the waveform is described as being no greater than about 1/6 the average amplitude of the positive pulse portion. The average amplitude of the positive pulse portion is described as being within the range of about 0.0001 to 0.01 volts per centimeter of tissue or cells, which corresponds to between about 0.1 and 10 microamperes per square centimeter of treated tissue and/or cells. An induced waveform having a positive pulse portion with a peak amplitude of between about 1 and 3 millivolts per centimeter of treated tissue, corresponding to 1 to 3 microamperes per square centimeter of treated tissue and/or cells, with the duration of each positive pulse portion being about 300 microseconds and the duration of each negative pulse portion of about 3300 microseconds, and a pulse repetition rate of about 72 Hertz, is stated to represent a preferred and optimum induced pulse signal for the treatment of bone disorders. A preferred treatment regime using Mode 1 type signals is described as having been found to be a minimum of 8 hours per day for a period of four months in difficult cases, and two weeks in less difficult cases.

The Ryaby, et al. patents, such as U.S. Pat. No. 4,315,503, also describe a Mode 2 type asymmetrical waveform, illustrated by FIG. 5b of the '503 patent, which waveform is induced in the tissue or cells. The Mode 2 type signal is applied in a pulse-train modality, which contains bursts (pulse groups) of asymmetrical waveforms. Each burst portion of the signal contains a series of pulses having positive and negative portions. Each positive pulse portion is described as including three segments 39', 40' and 41'. The peak negative amplitude of the negative pulse portion is stated as preferably not being more than about 40 times the peak amplitude of the positive pulse portion. The duration of each positive pulse portion is described as being at least about four times the duration of the following negative pulse portion. The pulse repetition rate of the pulses within the burst segment of the Mode 2 pulse train is described as possibly being between about 2,000 Hertz and 10,000 Hertz.

It is stated in the Ryaby, et al. patents, such as the '503 patent, that the average magnitude of the positive peak potential of the Mode 2 type signal should be within the range of about 0.00001 to 0.01 volts per centimeter of tissue and/or cells, which corresponds to about 0.01 to 10 microamperes per square centimeter of treated tissue and/or cells. It is further stated that the repetition rate of the burst segment should be within the range of about 5 to 15 Hertz for bone and other hard tissues. It is further described that each negative pulse portion within the burst segment of the pulse train should be of a duration no greater than about 50 microseconds and of an average amplitude no greater than 50 millivolts per centimeter of treated tissue and/or cells, corresponding to about 50 microamperes per square centimeter of treated tissue and/or cells.

The Ryaby, et al. patents further state that for the treatment of bone disorders using a Mode 2 type signal, an optimum induced positive pulse signal portion has a peak amplitude of between about 1 and 3 millivolts per centimeter of treated tissue, which corresponds to 1 to 3 microamperes per square centimeter of treated tissue and/or cells, with a duration of each positive pulse portion being about 200 microseconds and the duration of each of the negative pulse portions being about 30 microseconds, a pulse repetition rate of about 4,000 Hertz, a burst segment width of about 5 milliseconds, and a burst repetition rate of about 10 Hertz. The Ryaby et al. patents describe a test-coil procedure to obtain the magnitude of the signal applied, from which the scale of field strength, as used in the patents, corresponds to 65 Tesla per second for each millivolt per centimeter in the tissue.

Although the asymmetrical waveforms described in the Ryaby, et al. patents, and more specifically shown in FIGS. 5a and 5b of those patents, may be suitable to bring about the desired growth or repair of the tissues under treatment, such signals are difficult to reproduce accurately. Expensive equipment and complex circuitry are necessary in order to produce such signals. Such circuitry is shown in FIGS. 7 through 11 of Ryaby, et al. U.S. Pat. No. 4,315,503.

In addition, such equipment does not appear to be portable for certain uses of preferred signals, which limits the ability to apply the recommended signals to only those times spent in the hospital or confined at home. In the extreme case, if such signals are recommended to be applied for eight hours a day during a four month period, one can see how a patient is, for all practicality, confined to the place of treatment.

OBJECTS AND SUMMARY OF THE INVENTION

It is an object of the present invention to provide a method and apparatus for inducing a signal in living tissue to affect the growth, repair or maintenance behavior of the living tissue.

It is another object of the present invention to provide a method and apparatus for inducing a voltage or current signal in living bone tissue to help prevent osteoporosis or enhance new bone formation.

It is yet another object of the present invention to provide a method and apparatus for applying a signal to living tissue by surgically non-invasive direct inductive coupling.

It is a further object of the present invention to provide a method for inducing a time-varying signal in living tissue, which signal has an uncomplicated waveform which is easily reproducible.

It is yet another object of the present invention to provide apparatus for non-invasively inducing a voltage or current signal in tissue, which apparatus is simple in construction, inexpensive for the user to purchase and uncomplicated to use.

It is yet a further object of the present invention to provide apparatus for inducing a time-varying signal in tissue, which apparatus is portable and may be easily carried by a person undergoing treatment.

It is an additional object of the present invention to provide a method and apparatus for preventing osteoporosis or for enhancing new bone formation by non-invasively inducing a low power, low frequency signal in the bone tissue being treated.

It is yet another object of the present invention to overcome the disadvantage of the methods and apparatus disclosed in the Ryaby, et al. patents discussed previously.

In accordance with one form of the present invention, it has been found that the application of very low amplitude, symmetric time-varying magnetic fields to non-invasively induce electric currents and voltages in tissue, especially hard tissue such as bone, has the capability of countering the effects of osteoporosis and enhancing new bone formation.

More specifically, it has been found that magnetic fields which are symmetric in time, as for example sinusoidal waveforms, resulting in current and voltage signals induced in bone tissue at frequencies of between 1 Hertz and 1 k Hertz and at peak intensities corresponding to a peak value of the inducing time-varying magnetic field of between about 0.5 millitesla per second and about 5 Tesla per second, are capable of preventing a loss of bone mass due to conditions normally expected to result in this loss, that is, osteoporosis. The field strength used in the application of such signals is three orders of magnitude below that currently used in FDA approved signals.

Also, in accordance with the present invention, apparatus for non-invasively inducing a current or voltage in either hard or soft tissues of living systems is disclosed. The apparatus includes, in one form of the present invention, a multi-conductor ribbon cable with appropriate connectors on each end, which cable may be arranged such that, when the two connectors are coupled together, the multiple conductors of the cable form the equivalent of a single conductor solenoid coil of multiple turns. The ribbon cable is flexible, which allows it to be wrapped around any odd shaped limb so that it may be used to induce electrical currents and voltages in the limb for therapeutic treatment. The ribbon cable is wrapped around the limb such that the electric field induces a current or voltage longitudinally in the bone tissue of the limb.

The apparatus also includes a signal generator which is connected to the ribbon cable. The signal generator is preferably in the form of a low power, low frequency portable sine wave generator, which generator is connected to a power supply, preferably a portable battery power source.

These and other objects, features and advantages of the present invention will be apparent from the following detailed description of illustrative embodiments thereof, which is to be read in connection with the accompanying drawings.

DETAILED DESCRIPTION OF THE PREFERRED EMBODIMENTS

Figure 1:
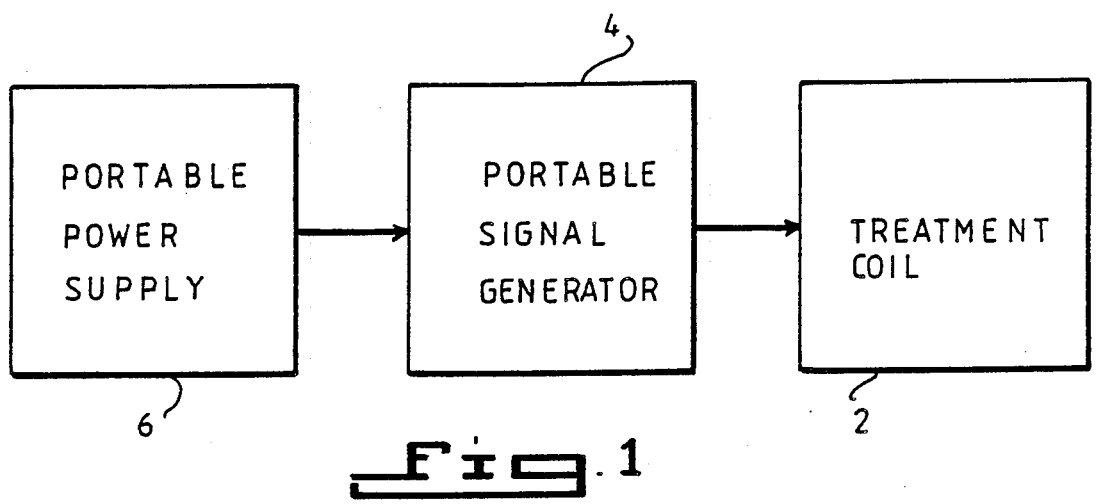
FIG. 1 is a block diagram of apparatus for noninvasively inducing a current and voltage in living tissue, constructed in accordance with one form of the present invention.

It is a common belief that the behavior of tissue cells can be modified by means of magnetic fields applied to the tissue cells. It is further known that if the magnetic field penetrates into the area of the tissue cells, and if the intensity of the magnetic field is varied with time, an induced current and concomitant change in electric potential in or around the cells of the tissue will result.

It was further believed that an asymmetrical waveform, such as disclosed in the Ryaby, et al. patents mentioned previously, would be the preferred form of an electrical potential and concomitant current signal to be impressed upon the tissues and/or cells undergoing treatment. As further stated in the Ryaby, et al. patents, and in particular in relation to the Mode 1-type of asymmetrical waveform applied to the tissue, a relatively high power was preferably used for treating the tissue, and a lower pulse potential would not result in a beneficial effect.

In accordance with the present invention, it has now been found that a low amplitude, time-varying waveform signal induced in living tissue will be effective in modifying beneficially and with uniform results the behavior of the living tissues and cells to which the induced signals are exposed. More specifically in accordance with the present invention, it has been found that a relatively low intensity, low frequency, substantially symmetrical, as for example sinusoidal, waveform signal induced in living tissues and/or cells will beneficially effect the growth, repair or maintenance behavior of the living tissues and/or cells. When the living tissue is bone, for example, the method of the invention has the capability of preventing or minimizing the effects of osteoporosis and enhancing new bone formation.

In accordance with the preferred embodiment of the present invention, a substantially symmetrical waveform signal is surgically non-invasively induced in the living tissue by using a treatment coil. The signal has a frequency of between about 1 Hertz and about 1 K Hertz; more preferably a frequency of between about 1 Hertz and about 100 Hertz; even more preferably, a frequency of between about 15 Hertz and about 75 Hertz; and optimally, a frequency of either 15 Hertz or 75 Hertz. Of course, it is envisioned that the signal induced in the tissue may be combinations of frequencies within the broader range.

The peak intensities of such time-varying signals are relatively low, and are about three orders of magnitude below that currently used in FDA approved signals. The peak intensities of the signals induced by the treatment coil correspond to a peak value of the inducing time-varying magnetic field of between about 0.5 millitesla per second and about 0.5 Tesla per second.

The preferred intensity depends on the particular frequency of the induced signal. For signals having a frequency of between about 1 Hertz and about 100 Hertz, the peak intensity of the signal corresponds to a peak value of the inducing time-varying magnetic field of between about 0.5 millitesla per second and about 0.5 Tesla per second. For signals having a frequency of between about 100 Hertz and about 1 K Hertz, the peak intensity of the signal corresponds to a peak value of the inducing time-varying magnetic field of between about 5 millitesla per second and about 5 Tesla per second. Thus, for a preferred signal having a frequency of 75 Hertz, the peak intensity of the signal corresponds to between about 0.5 millitesla per second and about 0.5 Tesla per second of the inducing time-varying magnetic field, and optimally corresponds to about 25 millitesla per second. At a signal frequency of 15 Hertz, the preferred peak intensity of the induced signal corresponds to a peak value of the inducing time-varying magnetic field of between about 0.5 millitesla per second and about 5 millitesla per second, and optimally corresponds to about 2.5 millitesla per second. For composite signals, i.e., signals comprising a plurality of frequency components, such as a square wave, the induced signals preferably have a significant fraction, that is, more than about 20%, of their induced intensity in a frequency range of between about 1 Hertz and about 1 K Hertz, which intensity corresponds to a peak value of the inducing time-varying magnetic field of between about 0.5 millitesla per second and about 5 Tesla per second.

Such signal levels tend to avoid damage to the tissue caused by the generation of heat and, as will be seen, enhances the applicability and portability of the apparatus for generating and applying such signals to the tissue under treatment.

The electrical fields induced in the living tissues at the low frequencies and intensities set forth above simulate the natural electric environment of the tissue when the environment has been disturbed. Normally, electrical fields are present in tissue due to ionic current flows generated by nerve and muscle cell activity, and by streaming current flows arising from stresses applied to charged connective tissues, and piezoelectric currents arising from the ferroelectric or crystalline properties of connective tissues such as bone. Thus, the bone remodels itself due to activity generated stress on the bone. The particular frequencies of the induced signal of the present invention emulate the natural frequencies of the body caused by stress, which induced signals will help prevent bone loss, such as caused by osteoporosis, and will help promote the development of new bone tissue.

The following examples detail the results of experiments using low frequency, low power, sinusoidal electric fields to regulate skeletal tissue cell activity in vivo using an established model of disuse osteoporosis.

EXAMPLE 1

An in vivo avian ulna preparation was used for the experiments. More specifically, the preparation consisted of the diophyseal region of an adult male turkey ulna, deprived of functional load bearing through proximal and distal metaphyseal osteotomies. The diophyseal face of each osteotomy was covered with a stainless steel cap to prevent bone reunion. While the diophyseal section of the ulna was deprived of mechanical function, the musculature, nutrient and nervous supplies remained undisturbed. The contralateral ulna was left untouched and served as the reference for estimating bone gain or loss. The ulnae of birds undergoing the same operation but left untreated served as controls.

Sinusoidal electric fields were induced in the bone preparation by the use of air core coils in an approximate Helmholtz configuration. Coils were applied to the wing for one hour per day, for an eight week period. Two frequencies were utilized, 15 and 75 Hertz, with magnetic flux densities adjusted to induce peak field intensities of approximately 4 microvolts per centimeter at the endosteal surface of the bone, resulting from a dB/dt of approximately 0.025 Tesla per second. At the end of the exposure period, both left and right ulnae were removed and cross-sectional areas of transverse histological sections were compared.

Results from this study show that, at both 15 and 75 Hertz signals, one hour per day of field exposure is capable of not only preventing the expected disuse bone loss (approximately a 12% reduction in bone) but also actually promoting new bone formation in a bone which is otherwise protected from any stress generated fields. The birds which were exposed to the 75 Hertz signal resulting from a maximum dB/dt of 0.025 Tesla per second exhibited an average bone cross sectional area which was about 20% greater than the controls. The birds exposed to a 15 Hertz signal resulting from a maximum dB/dt of 0.025 Tesla per second exhibited an average bone area which was about 40% greater than the controls through both endosteal and periosteal new bone formation.

EXAMPLE 2

The preparation consisted of the diaphysis of the adult turkey ulna deprived of functional load bearing by proximal and distal metaphyseal osteotomies. The diaphyseal face of each osteotomy was covered with a stainless steel cap which prohibited bony union. While the diaphysis was deprived of mechanical function, the musculature, nutrient and nervous supplies remained undisturbed. The contralateral ulna was left untouched, and served in the analysis as a reference for estimating bone gain or loss. The ulnae of birds undergoing the same operation but left untreated served as controls.

Three experimental sinusoidal signals were utilized. Signal A was a 75 Hertz sinusoidal signal at a level corresponding to about 0.2 Tesla per second. Signal B was a 75 Hertz sinusoidal signal at a level corresponding to about 0.025 Tesla per second. Signal C was a 15 Hertz sinusoidal signal at a level corresponding to about 0.025 Tesla per second. The field intensities of the signals induced measured at the endosteal surface of the ulna were on the order of 30 microvolts per centimeter for signal A, and approximately 4 microvolts per centimeter for signals B and C.

The sinusoidal signals were induced in the preparation using air core coils that were strapped to the wing of the animal in an approximate Helmholmtz configuration. The coils were connected directly to a remote signal generator, including a power amplifier, and coil current was monitored for the duration of the exposure period.

The isolated ulnae of ten birds were exposed to the magnetic fields for one hour per day, for an eight week period. At the end of the exposure period, the animals were euthanized and both right and left ulnae were removed, and cortical areas of transverse sections of the midshaft were compared.

For the ulna exposed to a 75 Hertz sinusoidal signal (Signal A), the cross sectional area of the ulna increased about 20% over the controls. The lower power 75 Hertz sinusoidal signal (Signal B) produced an average cross sectional area increase of about 20% over the controls. For the 15 Hertz sinusoidal signal (Signal C), the cross sectional area of the isolated ulna increased 40% as compared to the controls.

The results of the above examples show that the exogenous induction in bone of electric currents of frequencies below 1 K Hertz, and more specifically, below 100 Hertz, and derived from magnetic field intensities below 0.05 Tesla per second will modulate bone remodeling activity and may be used to prevent osteoporosis and promote new bone formation.

Apparatus constructed in accordance with the present invention for carrying out the method of applying such signals is illustrated by FIGS. 1 through 5 of the drawings.

More specifically, FIG. 1 shows in block diagram form one form of the apparatus, which basically comprises a treatment coil 2, and a signal generator 4 which is connected to the treatment coil 2 and which supplies to the coil a low power, symmetrical (ex., sinusoidal) signal, a comparable time-varying signal being induced by the coil in the tissue undergoing treatment. The signal generator 4 is further connected to a power source 6, which is preferably a battery power supply. The low power requirements and non-complex symmetrical signals used in the method of the present invention allow the apparatus to be formed in a portable unit that may be carried by the person or subject being treated.

Figure 2:
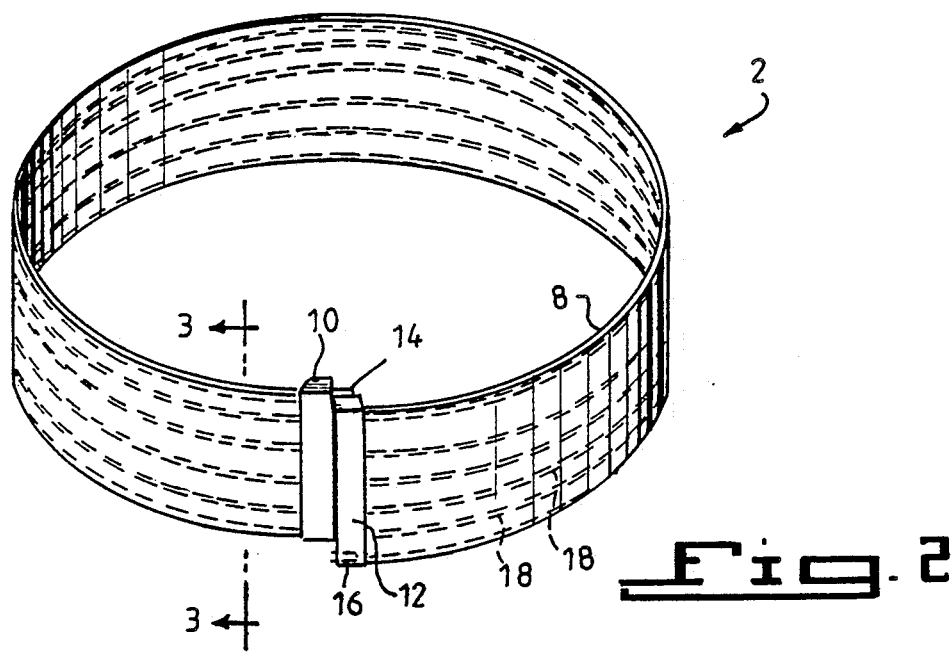
FIG. 2 is a perspective view of a multi-conductor flexible ribbon cable used in the apparatus illustrated by FIG. 1.
Figure 3:
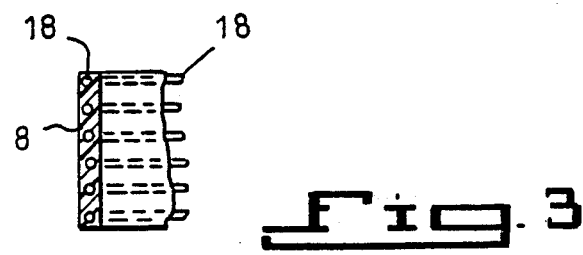
FIG. 3 is a transverse cross sectional view of the ribbon cable shown in FIG. 2, taken along line 3—3 of FIG. 2.
Figure 4:
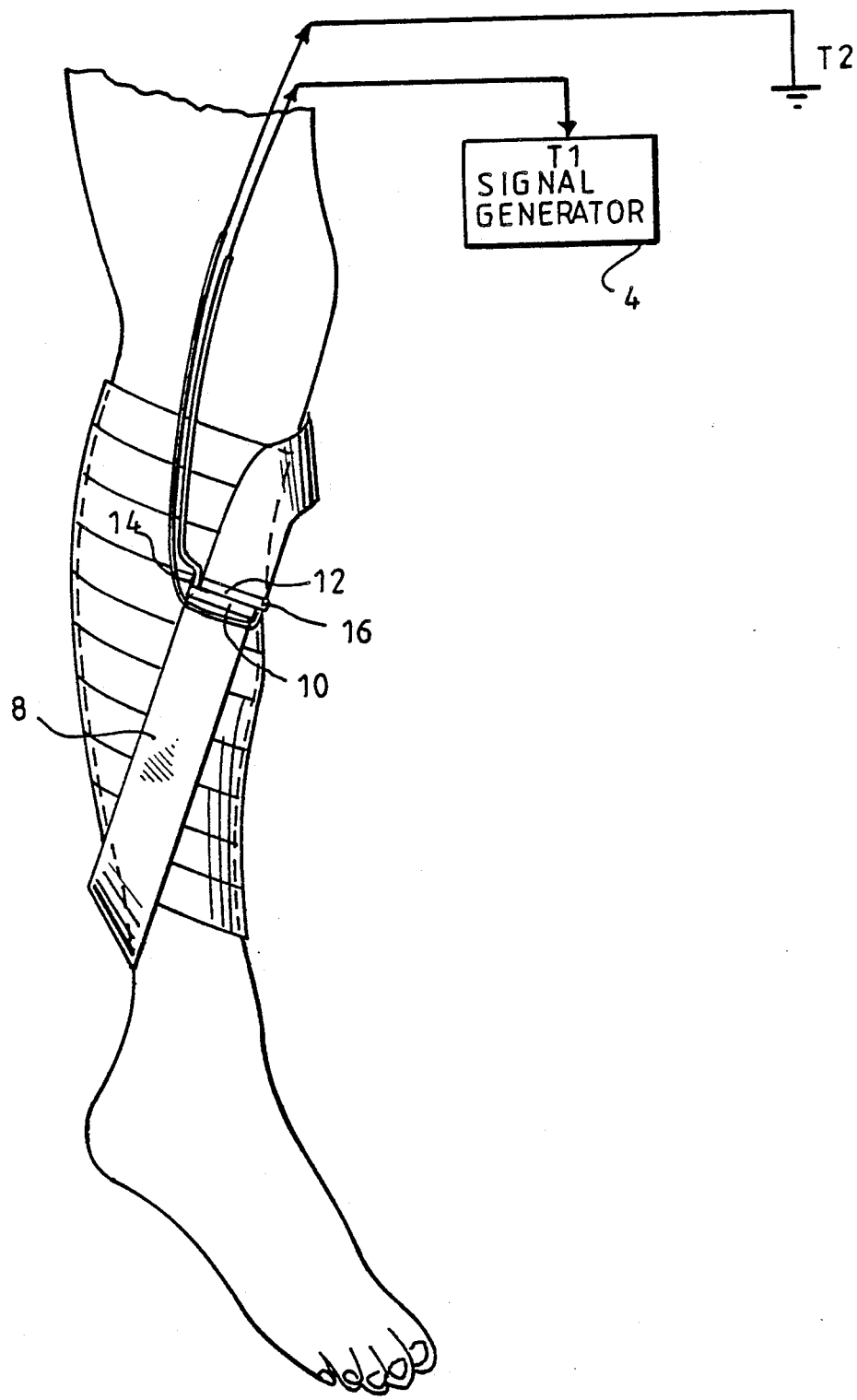
FIG. 4 is a side elevational view illustrating pictorially how the multi-conductor ribbon cable may be applied to a limb for inducing electrical currents or voltages longitudinally in the limb.

As shown in FIGS. 2-4, the treatment coil 2 is preferably in the form of a multi-conductor ribbon cable 8 with appropriate male and female connectors 10, 12 mounted on each end, the male connector 10 having a plurality of pins 14, and the female connector 12 having a plurality of plugs 16. A typical ribbon cable 8 which is suitable for use is manufactured by 3 M Company under Series No. 3000. The ribbon cable 8 is, of course, separate, independent insulated wire conductors 18 disposed in a parallel, side-by-side arrangement. However, when the male and female connectors 10, 12 are coupled together but are intentionally laterally misaligned so that the male connector pin 14 of any one or more individual conductors mates with a female connector plug 16 of another conductor, as illustrated by FIG. 2, the ribbon cable 8 forms the equivalent of a single conductor coil of multiple turns, which is used as the treatment coil 2.

If only one pin 14 and plug 16 of the mating male and female connectors 10, 12 are offset from each other, each wire conductor 18 of the multi-conductor ribbon cable will be connected to its next adjacent conductor so that all of the conductors are joined together in series to define the treatment coil. The unused pin 14 of the male connector 10 and the unused plug 16 of the female connector 12 are electrically connected to the output terminals (i.e., the signal output terminal T1, and the return or ground terminal T2) of the signal generator 4.

If the male and female connectors 10, 12 of the multi-conductor ribbon cable 8 are misaligned such that two pins 14 of the male connector 10 and two plugs 16 of the female connector 12, for example, are not connected to mating plugs and pins, and the output terminals (i.e., the signal terminal T1 and the ground terminal T2) of the signal generator 4 are connected to the second or inner pin from the end of the male connector 10 and to the second or inner plug from the opposite end of the female connector 12, only alternate conductors of the multi-conductor ribbon cable will be energized. Accordingly, the inductance of the coil 2 will be reduced to one quarter that of the coil defined by the cable arrangement where only one pin and plug are offset on each connector and, consequently, the field strength applied to the tissue under treatment will be effectively reduced.

For a further reduction in field strength and coil inductance, the male and female connectors 8, 10 may be offset laterally to a greater degree, such as by three pins 14 and plugs 16 or more. Thus, the intensity of the applied field may be easily adjusted using the same ribbon cable 8 as the treatment coil.

Another advantage of using a multi-conductor ribbon cable 8 as the treatment coil 2 is that the cable is very flexible and may be wrapped around an odd-shaped limb, as illustrated by FIG. 4, so as to be used to induce electrical currents and voltages longitudinally in the limb for therapeutic treatment. A longer version may be used to treat an entire limb. Also, the coil 2 defined by the wrapped multiconductor ribbon cable 8 is extremely lightweight and inexpensive to construct, and may be easily applied to the limb by the patient undergoing treatment.

Figure 5:
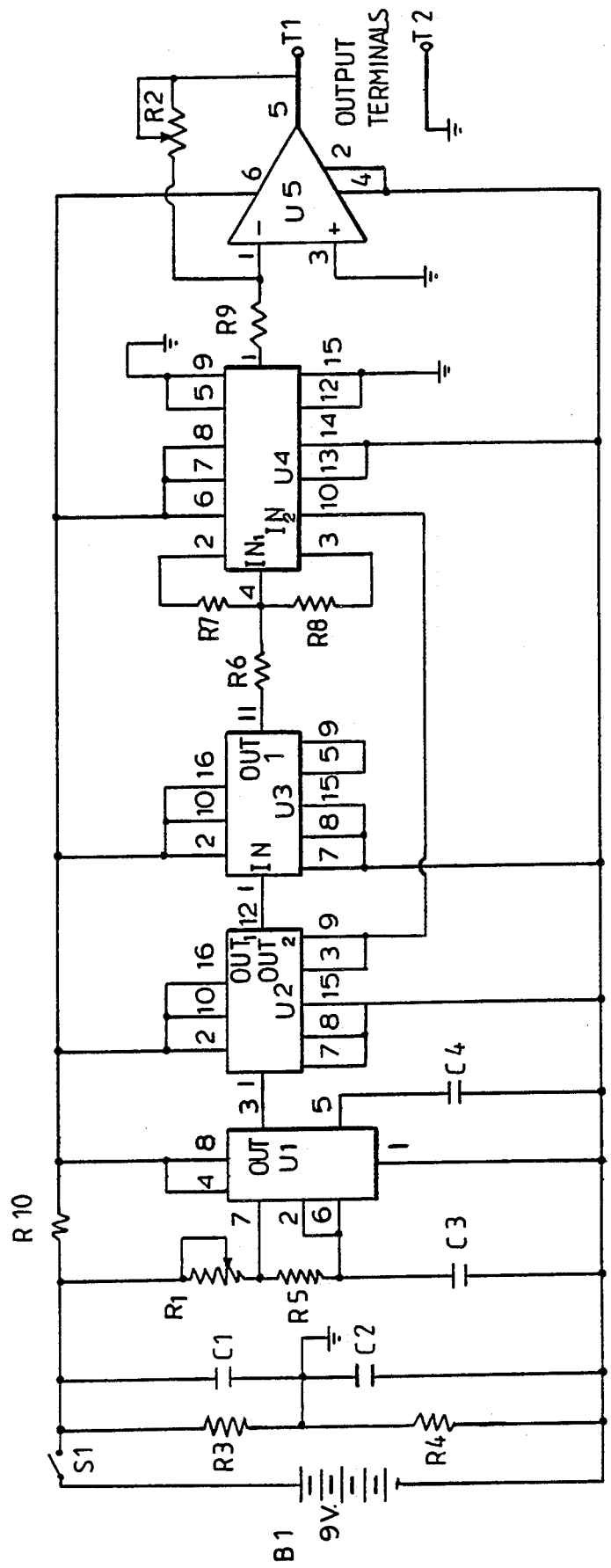
FIG. 5 is a schematic diagram of the signal generator of the apparatus illustrated in block diagram form in FIG. 1.

A preferred form of the signal generator 4 of the apparatus is shown schematically in FIG. 5. The signal generator 4 is a low powered design and includes a free running, astable multivibrator U1, a pair of BCD counters U2, U3 connected in series to each other and wired as down counters, the lead counter U2 being connected to an output of the multivibrator U1, a low pass filter U4 connected to an output of the end counter U3, and a driver/output buffer U5 connected to the output of the low pass filter U4. U1–U5 are preferably integrated circuits. Potentiometer R1 is provided for adjusting the frequency of the multivibrator U1, and potentiometer R2 is provided for adjusting the amplitude of the output signal of the driver U5.

A parts list for the circuit shown in FIG. 5 is provided below. Also, the pin numbers shown in FIG. 5 for integrated circuits U1–U5 relate to the parts specified in the list although, of course, it is envisioned that compo-

| PARTS LIST FOR CIRCUIT SHOWN IN FIG. 5 | |
|---|---|
| Reference Designation | Part Description |
| B1 | 9 V battery |
| S1 | Single pole, single throw switch |
| U1 | 555 timer, National Semiconductor |
| U2 | 4518 BCD counter, Texas Instruments |
| U3 | 4518 BCD counter, Texas Instruments |
| U4 | ¦MF10 Universal active filter, National Semiconductor |
| U5 | LM 13080 Operational amplifier, National Semiconductor |
| R1 | 1M ohm potentiometer |
| R2 | 10 k ohm potentiometer |
| R3 | 10 k ohm resistor |
| R4 | 10 k ohm resistor |
| R5 | 1 k ohm resistor |
| R6 | 10 k ohm resistor |
| R7 | 10 k ohm resistor |
| R8 | 10 k ohm resistor |
| R9 | 10 k ohm resistor |
| R10 | 220 ohm resistor |
| C1 | .1 uf capacitor |
| C2 | .1 uf capacitor |
| C3 | 470 pf capacitor |
| C4 | .01 uf capacitor |

The output signal on output terminal T1 (output terminal T2 is ground or return) is a symmetrical waveform, for example, a sinusoidal signal, which is also preferably symmetric about the 0 volt axis. The output signal is provided to the treatment coil (i.e., terminals T1 and T2 are connected to a free pin 14 and plug 16 of the ribbon cable connectors 10, 12 shown in FIG. 2).

The power source is preferably a battery power supply B1 which, for the circuit shown in FIG. 5, is a 9 volt battery. The battery is connected to the signal generator through a power switch S1.

Battery B1 is connected in series with power switch S1. Resistor R3 and capacitor C1 are in parallel, and resistor R4 and capacitor C2 are in parallel. The parallel combination of R3 and C1, and R4 and C2 are connected together in series between switch S1 and the negative side of battery B1, and their common connection is grounded. This combination provides a positive and negative 4.5 volts with respect to ground.

Potentiometer R1 is connected in series with resistor R5 which, in turn, is connected in series with capacitor C3. R1, R5 and C3 determine the frequency of the output signal of multivibrator U1. If a 555 timer is used as multivibrator U1, pin 5 of the 555 timer is connected to a capacitor C4.

The output of the multivibrator U1 is connected to the input of counter U2, whose lowest frequency output OUT 1 is connected to the input of counter U3. An output OUT 1 of counter U3 is connected through resistor R6 to one input IN 1 of low pass filter U4, which input is also connected to resistors R7 and R8. A higher frequency output OUT 2 of counter U2 (the frequency of the signal on OUT 2 is about 50 times that of the signal on OUT 1 of counter U3) is connected to the sampling rate input IN 2 of filter U4. The output of the filter U4 is connected to the inverting input of operational amplifier U5 through input resistor R9. Potentiometer R2 acts as a feedback resistor for driver U5. R10 is provided for decoupling.

Because of its compact size, the signal generator 4 and power supply 6 may be carried by the person undergoing treatment and may be attached to a belt carried around the person's waist or, more preferably, around the limb undergoing treatment.

The method of the present invention not only helps to prevent osteoporosis, but also may be used to enhance new bone formation. In other words, it is envisioned that the method may be used not only for therapeutic treatment of bone and tissue disorders, but also for the prevention of bone loss due to the effects of aging or inactivity.

Because of the portable nature of the apparatus and the non-constricting form of the treatment coil, it is envisioned that the device may be worn daily by a person for 15 minutes or so, one or more times a day, to supplement a person's program of daily exercise in order to prevent bone loss and actually promote bone formation without restricting a person's movement to any significant degree. Longer periods, such as 1 to 8 hours per day, will also provide beneficial results.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed is:

1. A surgically non-invasive method of treating living tissues and/or cells comprising the step of:
   inducing, by a time-varying magnetic field, a time varying electric field which in turn induces voltage and concomitant current signals within said tissue and/or cells, 2. A method as defined by claim 1, wherein the frequency of the signals is between about 15 Hertz and about 75 Hertz, and wherein the induced time varying electric field has a peak intensity of between about 0.08 microvolts per centimeter and about 80 microvolts per centimeter.

3. A method as defined by claim 1, wherein the frequency of the signals is about 15 Hertz, and wherein the induced time varying electric field has a peak intensity of between about 0.08 microvolts per centimeter and about 80 microvolts per centimeter.

4. A method as defined by claimed 1, wherein the frequency of the signals is about 75 Hertz, and wherein the induced time varying electric field has a peak intensity of between about 0.08 microvolts per centimeter and about 80 microvolts per centimeter.

5. A method as defined by claim 1, wherein the peak intensity of the induced time-varying electric field is about 4 microvolts per centimeter, and the frequency of the voltage and current signals is about 75 Hertz.

6. A method as defined by claim 1, wherein the peak intensity of the induced time-varying electric field is between about 0.8 microvolts per centimeter and about 0.8 microvolts per centimeter, and the frequency of the voltage and current signals is about 15 Hertz.

7. A method as defined by claim 1, wherein the peak intensity of the induced time-varying electric field is about 0.4 microvolts per centimeter, and the frequency of the voltage and current signals is about 15 Hertz.

8. A surgically non-invasive method of treating living tissues and/or cells comprising the step of:
   inducing, by a time-varying magnetic field, a time-varying electric field which in turn induces voltage and concomitant current signals within said tissue and/or cells, wherein said voltage and current signals have a significant fraction, that is, more than about 20%, of their power in a frequency range of between about 1 Hertz and about 1 KHertz, which power corresponds to a peak value of the induced time-varying electric field of between 0.08 microvolts per centimeter and about 800 microvolts per centimeter.

* * * * *

UNITED STATES PATENT AND TRADEMARK OFFICE
CERTIFICATE OF CORRECTION

PATENT NO. : 4,993,413
DATED : February 19, 1991
INVENTOR(S) : McLeod et al.

It is certified that error appears in the above-identified patent and that said Letters Patent is hereby corrected as shown below:

In Column 6, Lines 11 & 15, "in vivo" should read --*in vivo*--.

In Column 10, Claim 1 should read as follows:

--A surgically non-invasive method of treating living tissue and/or cells comprising the step of inducing, by a time varying magnetic field, a time varying electric field which in turn induces voltage and concomitant current signals within said tissue and/or cells, wherein said voltage and said current signals are substantially symmetric and have a frequency of between about 1 Hertz and 1 K Hertz and wherein the induced time-varying electric field has a heat intensity of between about .08 microvolts per centimeter and about 80 microvolts per centimeter when the voltage and current signals have a frequency of between about 1 Hertz and about 100 Hertz, and has a peak intensity of between about .8 microvolts per centimeter and 800 microvolts per centimeter when the voltage and current signals have a frequency of about 100 Hertz and about 1 K Hertz.--

Signed and Sealed this

Tenth Day of November, 1992

*Attest:*

DOUGLAS B. COMER

*Attesting Officer*    *Acting Commissioner of Patents and Trademarks*